(12) United States Patent
Fujii

(10) Patent No.: US 9,569,841 B2
(45) Date of Patent: Feb. 14, 2017

(54) MEDICAL IMAGE PROCESSING APPARATUS AND MEDICAL IMAGE GENERATION METHOD

(71) Applicant: HITACHI, LTD., Chiyoda-ku, Tokyo (JP)

(72) Inventor: Nobuhiko Fujii, Mitaka (JP)

(73) Assignee: HITACHI, LTD., Tokyo (JP)

( * ) Notice: Subject to any disclaimer, the term of this patent is extended or adjusted under 35 U.S.C. 154(b) by 55 days.

(21) Appl. No.: 14/440,266

(22) PCT Filed: Oct. 25, 2013

(86) PCT No.: PCT/JP2013/079005
§ 371 (c)(1),
(2) Date: May 1, 2015

(87) PCT Pub. No.: WO2014/069374
PCT Pub. Date: May 8, 2014

(65) Prior Publication Data
US 2015/0317791 A1 Nov. 5, 2015

(30) Foreign Application Priority Data
Nov. 1, 2012 (JP) .................................. 2012-241558

(51) Int. Cl.
*G06T 7/00* (2006.01)
*G06T 5/00* (2006.01)
(Continued)

(52) U.S. Cl.
CPC ........... *G06T 7/0012* (2013.01); *A61B 8/5269* (2013.01); *A61B 8/5276* (2013.01); *G01R 33/56* (2013.01);
(Continued)

(58) Field of Classification Search
CPC .......... G06T 7/0012; G06T 5/00; G06T 5/002; G06T 5/009; G06T 5/20; G06T 7/0024; G06T 9/00; G06T 11/60; G06T 3/4038; G06T 2207/10132; G06T 2207/20182; G06T 2207/20212; G06T 2207/20221; G06T 2207/20024; G06T 2207/30048; A61B 8/5269; A61B 8/5276; A61B 8/461; A61B 8/469; A61B 6/5229; A61B 6/5235; A61B 6/5241; A61B 6/5246; A61B 6/5247; A61B 8/5253; A61B 6/5258; A61B 8/5261; G06K 9/40; H04N 5/357; H04N 1/409; G01R 33/56; G01R 33/5635
See application file for complete search history.

(56) References Cited

U.S. PATENT DOCUMENTS 5,812,195 A * 9/1998 Zhang .................. H04N 19/503
375/240.16
6,211,911 B1 * 4/2001 Komiya ................ H04N 1/195
348/218.1
(Continued)

FOREIGN PATENT DOCUMENTS

| JP | 2011125690 A | 6/2011 |
| WO | 2008010375 A1 | 1/2008 |
| WO | 2009128213 A1 | 10/2009 |

OTHER PUBLICATIONS

Nov. 19, 2013 International Search Report issued in Japanese Application No. PCT/JP2013/079005.

*Primary Examiner* — Manav Seth
(74) *Attorney, Agent, or Firm* — Oliff PLC

(57) ABSTRACT

The present invention is a medical image processing apparatus which acquires medical image data on a diagnosing object, the apparatus including: a signal enhancement processing part which performs a signal enhancement process
(Continued)

on the medical image data; a noise removal part which performs a noise removal process on the medical image data; a first signal compression processing part which compresses the medical image data on which the signal enhancement process and the noise removal process have been performed; a second signal compression processing part which compresses the medical image data; and a synthesis processing part which synthesizes the medical image data having been compressed in the first signal compression processing part and the medical image data having been compressed in the second signal compression processing part.

14 Claims, 10 Drawing Sheets

(51) Int. Cl.
| | |
|---|---|
| G06T 5/20 | (2006.01) |
| G06T 11/60 | (2006.01) |
| A61B 8/08 | (2006.01) |
| G06K 9/40 | (2006.01) |
| H04N 1/409 | (2006.01) |
| G01R 33/56 | (2006.01) |
| H04N 5/357 | (2011.01) |
| A61B 8/00 | (2006.01) |

(52) U.S. Cl.
CPC ............... *G06K 9/40* (2013.01); *G06T 5/002* (2013.01); *G06T 5/009* (2013.01); *G06T 5/20* (2013.01); *G06T 11/60* (2013.01); *H04N 1/409* (2013.01); *H04N 5/357* (2013.01); *A61B 8/461* (2013.01); *A61B 8/469* (2013.01); *G06T 2207/10132* (2013.01); *G06T 2207/20182* (2013.01); *G06T 2207/20208* (2013.01); *G06T 2207/20221* (2013.01)

(56) References Cited

U.S. PATENT DOCUMENTS

| | | | | |
|---|---|---|---|---|
| 7,397,851 | B2* | 7/2008 | Roman | H04N 19/132 |
| | | | | 375/240 |
| 7,404,797 | B2* | 7/2008 | Azuma | A61B 8/08 |
| | | | | 600/437 |
| 9,230,354 | B2* | 1/2016 | O'Connor | A61B 6/482 |
| 9,311,695 | B2* | 4/2016 | Takahashi | A61B 6/5205 |
| 2004/0008901 | A1* | 1/2004 | Avinash | G06T 3/4007 |
| | | | | 382/260 |
| 2010/0022878 | A1 | 1/2010 | Azuma et al. | |
| 2011/0118599 | A1 | 5/2011 | Osumi | |
| 2011/0125030 | A1 | 5/2011 | Bai et al. | |

* cited by examiner

FIG. 5

| INTERNAL TABLE | | SIGNAL ENHANCEMENT LEVEL | | |
|---|---|---|---|---|
| | | 0 | 1 | 2 |
| SYNTHETIC RATIO | α | 0.3 | 0.4 | 0.5 |
| | β | 0.8 | 0.8 | 0.8 |

FIG. 9

| INTERNAL TABLE | | SIGNAL ENHANCEMENT LEVEL | | |
|---|---|---|---|---|
| | | 0 | 1 | 2 |
| SYNTHETIC RATIO | α1 | 0.2 | 0.25 | 0.3 |
| | α2 | 0.1 | 0.15 | 0.2 |
| | β | 0.8 | 0.7 | 0.7 |

MEDICAL IMAGE PROCESSING APPARATUS AND MEDICAL IMAGE GENERATION METHOD

TECHNICAL FIELD

The present invention relates to a medical image processing apparatus and a medical image generation method, and more particularly to a medical image processing apparatus and a medical image generation method for displaying high-contrast medical images.

BACKGROUND ART

An ultrasound diagnostic apparatus, which is a medical image processing apparatus, sends ultrasonic waves to a diagnosing object by means of an ultrasound probe and receives a reflection echo from the diagnosing object to construct an ultrasound image using a reflection echo signal. However, the ultrasound image contains speckle noise due to signal scattering or interference in a heterogeneous medium inside a living body and electric noise generated inside the apparatus.

In an ultrasound image of the heart, for example, conspicuous noise inside the heart chamber causes degradation of the image quality. In addition, conspicuous noise inside the heart chamber blurs the boundary between the heart chamber and the cardiac muscle, which adversely affects the diagnosis.

In image processing which is employed as means for removing noise from ultrasound images, linear filters including a low-pass filter and nonlinear filters including a median filter and a minimum value filter are well known.

On the other hand, in ultrasound images of the heart, image enhancement in the cardiac muscle is also required. As signals in the cardiac muscle are enhanced, the movement of the heart becomes easier to recognize, which favorably affects the diagnosis.

In image processing which is employed as means for enhancing signals in ultrasound images, nonlinear filters including a maximum value filter are well known.

Meanwhile, a technique for improving the image quality of ultrasound images which performs both of noise removal and signal enhancement as described above has also been disclosed.

CITATION LIST

Patent Literature

Patent Literature 1: International Publication No. WO 2009/128213

SUMMARY OF INVENTION

Technical Problem

However, in the conventional ultrasound diagnostic apparatus which is a medical image processing apparatus, there is a concern that, for example, when noise inside the heart chamber is removed from an ultrasound image of the heart, signals of a cardiac muscle part may also be removed, so that the boundary between the heart chamber and the cardiac muscle may become blur. On the other hand, there is a problem that, when signals of the cardiac muscle part are enhanced, noise inside the heart chamber is also enhanced. Moreover, in the medical image processing apparatus of Patent Literature 1, it is difficult to construct a high-contrast ultrasound image while the dynamic range remains almost the same.

The present invention provides a medical image processing apparatus and a medical image generation method for constructing high-contrast medical images in which noise can be removed while signals in a region of attention can be enhanced.

Solution to Problem

The present invention is a medical image processing apparatus which acquires medical image data on a diagnosing object, the apparatus including: a signal enhancement processing part which performs a signal enhancement process on the medical image data; a noise removal part which performs a noise removal process on the medical image data; a first signal compression processing part which compresses the medical image data on which the signal enhancement process and the noise removal process have been performed; a second signal compression processing part which compresses the medical image data; and a synthesis processing part which synthesizes the medical image data compressed in the first signal compression processing part and the medical image data compressed in the second signal compression processing part.

According to this configuration, it is possible to construct high-contrast medical images in which noise can be removed while signals in a region of attention can be enhanced.

Advantageous Effects of Invention

The present invention can provide a medical image processing apparatus and a medical image generation method which can construct high-contrast medical images in which noise can be removed while signals in a region of attention can be enhanced.

BRIEF DESCRIPTION OF DRAWINGS

FIG. 5 is one example of an internal table which stores two synthetic ratios (weighting factors) corresponding to respective signal enhancement levels.

FIG. 9 is one example of an internal table which stores three synthetic ratios (weighting factors) corresponding to respective signal enhancement levels.

DESCRIPTION OF EMBODIMENTS

First Embodiment

Figure 1:
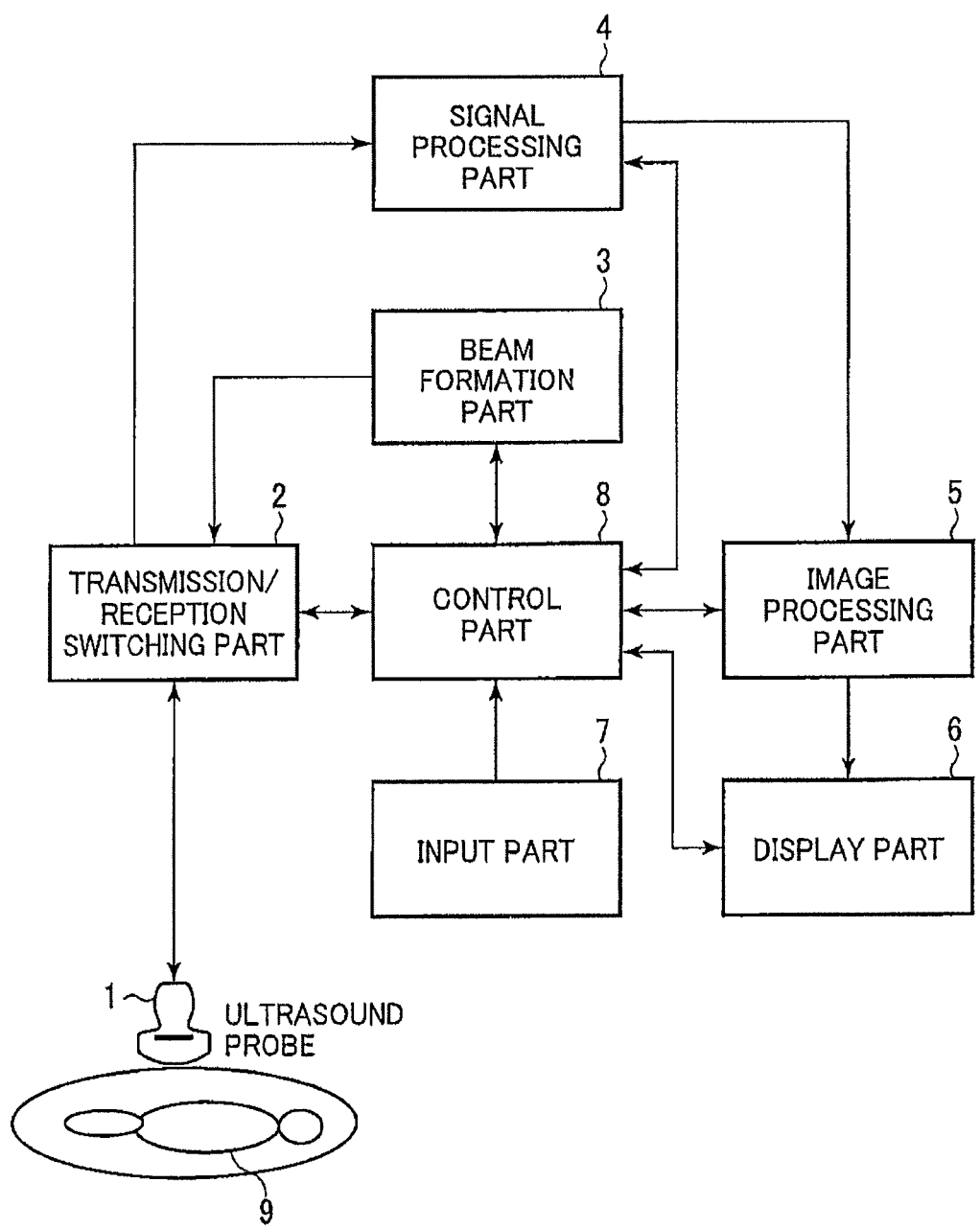
FIG. 1 is a block diagram showing one example of an ultrasound diagnostic apparatus which is a medical image processing apparatus of a first embodiment of the present invention.

In the following, a medical image processing apparatus of a first embodiment of the present invention will be described using the drawings. FIG. 1 is a block diagram showing one example of an ultrasound diagnostic apparatus which is the medical image processing apparatus of the first embodiment of the present invention.

The ultrasound diagnostic apparatus includes an ultrasound probe 1, a transmission/reception switching part 2, a beam formation part 3, a signal processing part 4, an image processing part 5, a display part 6, an input part 7, and a control part 8.

The ultrasound probe 1 transmits an ultrasonic beam to an object to be imaged and receives a reflection echo signal from the object to be imaged. The ultrasound probe 1 may be a one-dimensional ultrasound probe having a structure in which transducer elements are arrayed in m channels in the major axis direction of the ultrasound probe, or may be a two-dimensional ultrasound probe having a structure in which transducer elements are arrayed in k channels in the minor axis direction in addition to the major axis direction. Moreover, the ultrasound probe 1 may have a transducer formed of a piezoelectric element, or may have a transducer formed of a semiconductor called cMUT (Capacitive Micromachined Ultrasonic Transducer: IEEE Trans. Ultrason. Ferroelect. Freq. Contr. Vol 45 pp. 678-690 May 1998 etc.).

The transmission/reception switching part 2 switches the ultrasound probe 1 between functions of transmitting/receiving ultrasonic waves. When the ultrasound probe 1 is functioning for transmission, the transmission/reception switching part 2 supplies a transmission signal from the beam formation part 3 to the ultrasound probe 1. When the ultrasound probe 1 is functioning for reception, the transmission/reception switching part 2 receives a reflection echo signal from a diagnosing object 9 and outputs it to the signal processing part 4.

The beam formation part 3 forms a signal with which the ultrasound probe 1 sends an ultrasonic beam to the diagnosing object 9. The beam formation part 3 can also focus a sending beam or a receiving beam in the minor axis direction by varying a delay time which is given to each of transducer elements (1 to k channels) in the minor axis direction of the ultrasound probe 1. The beam formation part 3 functions to weight ultrasonic transmission signals by varying the amplitude of the ultrasonic transmission signals which are given to the respective transducer elements in the minor axis direction, and to weight ultrasonic reception signals by varying the amplification factor or the attenuance of the ultrasonic reception signals which are received from the respective transducer elements in the minor axis direction. The beam formation part 3 can perform aperture control by driving each of the transducer elements in the minor axis direction.

The signal processing part 4 amplifies and digitizes a reflection echo signal and generates ultrasound image data 10 (medical image data). The image processing part 5 performs image processing on the ultrasound image data 10.

The display part 6 displays an ultrasound image on which image processing has been performed by the image processing part 5. For example, the display part 6 includes a liquid crystal monitor. As long as ultrasound images (medical images) are displayed and medical images which can be diagnosed by an operator are displayed in the display part 6, any display technology, whether analog output or digital output, is included in this embodiment.

The input part 7 inputs control parameters of the ultrasound diagnostic apparatus such as parameters for imaging ultrasound images. The input part 7 may include at least one operation device such as a keyboard, a trackball, or a mouse.

The control part 8 controls such that each of the transmission/reception switching part 2, the beam formation part 3, the signal processing part 4, the image processing part 5, and the display part 6 functions on the basis of parameters (parameters for imaging ultrasound image data etc.) input through the input part 7. The control part 8 may be configured of a computer system centered around a central processing unit.

Figure 2:
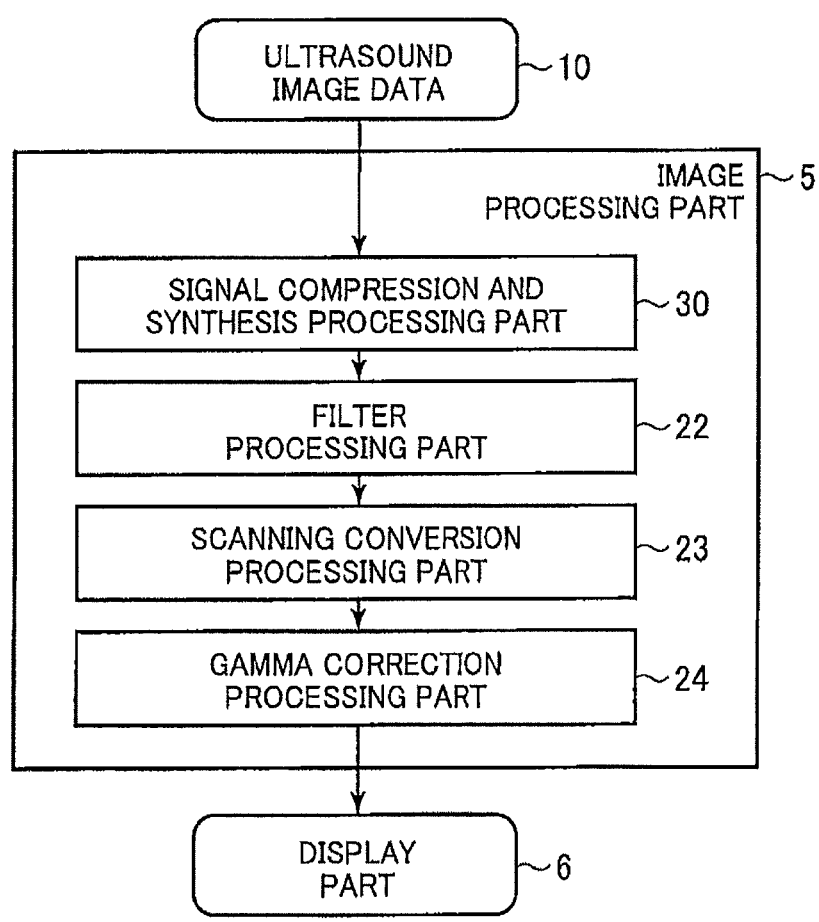
FIG. 2 is a block diagram showing a configuration example of an image processing part.

Next, the main configuration of the image processing part 5 of FIG. 1 will be described using FIG. 2. FIG. 2 is a block diagram showing a configuration example of the image processing part 5.

The image processing part 5 includes a signal compression and synthesis processing part 30, a filter processing part 22, a scanning conversion processing part 23, and a gamma correction processing part 24, and performs respective processes on the ultrasound image data 10 (medical image data).

The signal compression and synthesis processing part 30 compresses the dynamic range of ultrasonic reception signals which are as enormous as $2^{20}$, for example, into a relatively small dynamic range, and synthesizes a plurality of pieces of compressed ultrasound image data (medical image data). Signal compression using a logarithmic function, an exponential function, a sigmoid function, etc. is available.

The filter processing part 22 performs an enhancement process, for example, aimed at sharpening a boundary.

When the ultrasound probe 1 is a convex type, for example, the scanning conversion processing part 23 converts the rectangular ultrasound image data 10 into a fan-shaped two-dimensional ultrasound image.

The gamma correction processing part 24 corrects the display gradation of pixels of an image, which has undergone a scanning conversion process by the scanning conversion processing part 23, by means of a gamma curve which determines the domain and the range of the pixels.

Figure 3:
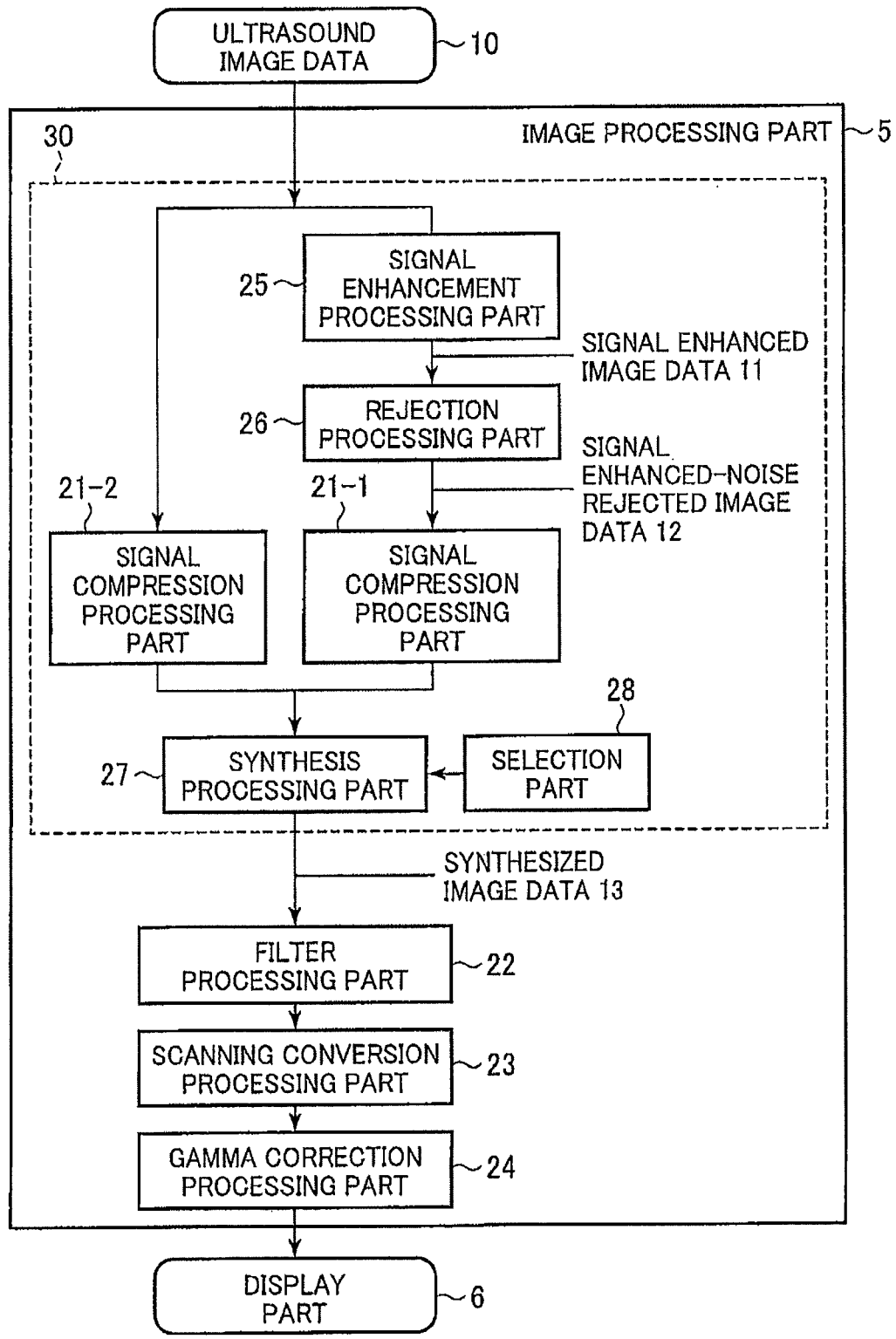
FIG. 3 is a view showing a configuration example of a signal compression and synthesis processing part of this embodiment.

FIG. 3 is a view showing a configuration example of the signal compression and synthesis processing part 30 of this embodiment. The medical image processing apparatus of this embodiment is an ultrasound diagnostic apparatus (medical image processing apparatus) which acquires medical image data on a diagnosing object, and includes: a signal enhancement processing part 25 which performs a signal enhancement process on the medical image data (ultrasound image data 10); a rejection processing part (noise removal part) 26 which performs a noise removal process on the medical image data (signal enhanced image data 11); a first signal compression processing part 21-1 which compresses the medical image data (signal enhanced-noise rejected image data 12) on which the signal enhancement process and the noise removal process have been performed; a second signal compression processing part 21-2 which compresses the medical image data (ultrasound image data 10); and a synthesis processing part 27 which synthesizes the medical image data having been compressed in the first signal compression processing part 21-1 and the medical image data having been compressed in the second signal compression processing part 21-2. In addition, the medical image processing apparatus of this embodiment includes the filter processing part 22, the scanning conversion processing part 23, and the gamma correction processing part 24 similar to those of FIG. 2.

In this embodiment, the first signal compression processing part 21-1 compresses the medical image data (signal enhanced-noise rejected image data 12) on which the signal enhancement process has been performed and thereafter the noise removal process has been performed. The second signal compression processing part 21-2 compresses the medical image data (ultrasound image data 10) on which the signal enhancement process and the noise removal process are not performed.

As shown in FIG. 3, the signal enhancement processing part 25 performs the signal enhancement process on the ultrasound image data 10. The signal enhancement process performed in the signal enhancement processing part 25 is executed using a maximum value filter etc.

Next, the rejection processing part 26 performs a rejection process, intended as a noise removal process, on the signal enhanced image data on which the signal enhancement process has been performed in the signal enhancement processing part 25. The rejection process (noise removal process) may be a rejection by "zeroing" values equal to or lower than a threshold value, or a rejection by differentiation. For the rejection process (noise removal process), linear filters including a low-pass filter or nonlinear filters including a minimum value filter may be used.

In the case of medical image data on the heart, for example, since the main part from which noise should be removed is the inside of the heart chamber, the rejection processing part 26 can automatically calculate a threshold value, which is set for the rejection process (noise removal process), by detecting the mean value, the median value, etc. of the luminance inside the heart chamber.

The first signal compression processing part 21-1 compresses the medical image data (signal enhanced-noise rejected image data 12) on which the signal enhancement process has been performed and thereafter the noise removal process has been performed. In FIG. 3, the medical image data, on which the signal enhancement process has been performed, is represented by the signal enhanced image data 11, and the medical image data, on which the signal enhancement process has been performed and thereafter the noise removal process has been performed, is represented by the signal enhanced-noise rejected (noise removed) image data 12. The second signal compression processing part 21-2 directly inputs and compresses the ultrasound image data 10.

In this embodiment, the first signal compression processing part 21-1 and the second signal compression processing part 21-2 compress the medical image data (ultrasound image data 10 and signal enhanced-noise rejected image data 12) by the same compression method and at the same compression ratio.

After the signal compression process by the first signal compression processing part 21-1 and the second signal compression processing part 21-2, the synthesis processing part 27 performs an image synthesis process on each piece of the medical image data on which the signal compression process has been performed. In this embodiment, the synthesis processing part 27 multiplies the medical image data (signal enhanced-noise rejected image data 12), which has been compressed in the first signal compression processing part 21-1, by a first weighting factor, and multiplies the medical image data (ultrasound image data 10), which has been compressed in the second signal compression processing part, by a second weighting factor, to thereby synthesize the medical image data having been compressed in the first signal compression processing part 21-1 and the medical image data having been compressed in the second signal compression processing part 21-2 and generate synthesized image data 13.

When the synthesized image data 13 is "y", the signal enhanced-noise rejected image data 12 is "$x_{e+r}$", and the ultrasound image data 10 is "x", the synthesis processing is expressed by the formula (1).

$$Y = \alpha \cdot x_{e+r} + \beta \cdot x \tag{1}$$

Here, in the formula (1), $\alpha$ denotes a synthetic ratio (first weighting factor) of the signal enhanced-noise rejected image data 12, and $\beta$ denotes a synthetic ratio (second weighting factor) of the ultrasound image data 10 which is the original image.

Figure 4:
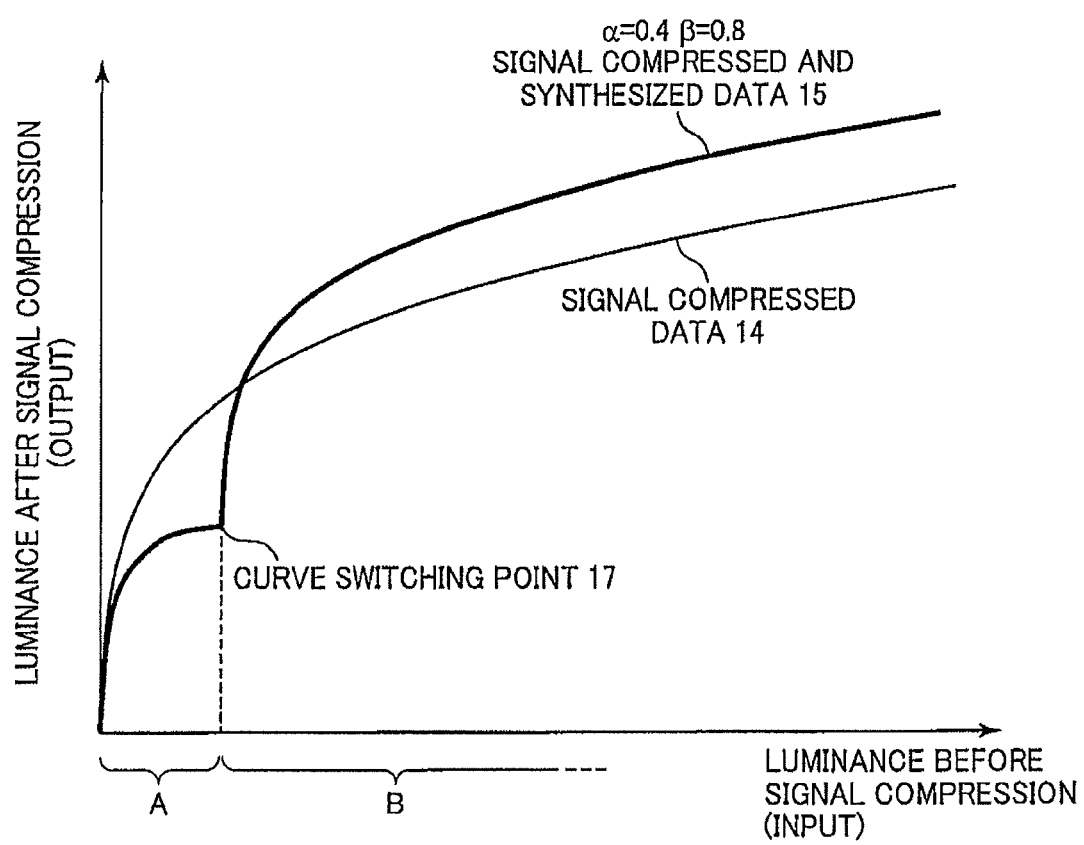
FIG. 4 is an example of comparison between signal compressed data and signal compressed and synthesized data.

FIG. 4 is an example of comparison between the signal compressed data 14, resulting from directly performing the signal compression process on the ultrasound image data 10, and the signal compressed and synthesized data 15 on which the signal compression process by the first signal compression processing part 21-1 and the second signal compression processing part 21-2 has been performed and the synthesis process has been performed with the synthetic ratio (first weighting factor) $\alpha$ being "0.4" and the synthetic ratio (second weighting factor) $\beta$ being "0.8". FIG. 4 shows the signal compressed data 14 and the signal compressed and synthesized data 15 on both of which the signal compression process has been performed using logarithmic compression.

As shown in FIG. 4, compared with the signal compressed data 14, the signal compressed and synthesized data 15 is lower in luminance of output (after signal compression) than the signal compressed data 14 in the range A where the luminance of input (before signal compression) is low, and is higher in luminance of output (after signal compression) than the signal compressed data 14 in the range B where the luminance of input (before signal compression) is high, and it can be seen that the signal compressed and synthesized data 15 is a high-contrast output. That is, the synthesis processing part 27 adjusts (increases) the synthetic ratio (first weighting factor) $\alpha$ such that, in a region of attention (e.g., the range B) of the diagnosing object 9, the luminance of the medical image data (signal compressed and synthesized data 15) synthesized by the synthesis processing part 27 becomes higher than the luminance of the medical image data (signal compressed data 14) on which the signal enhancement process and the rejection process (noise removal process) are not performed. The synthesis processing part 27 may adjust (reduce) the synthetic ratio (second weighting factor) $\beta$ such that, in parts (parts other than the region of attention) having the luminance lower than the luminance of the region of attention of the diagnosing object 9 (e.g., in the range A), the luminance of the medical image data (signal compressed and synthesized data 15) synthesized by the synthesis processing part 27 becomes lower than the luminance of the medical image data (signal compressed data 14) which has been compressed without the signal enhancement process and the noise removal process performed on it.

Since a curve switching point 17 found in the signal compressed and synthesized data 15 is equivalent to the threshold value of the rejection process (noise removal process) by the rejection processing part (noise removal part) 26, it is possible to change the range A, where the luminance is desired to be lower (or the range B where the luminance is desired to be higher) than that of the signal compressed data 14, by changing the threshold value of the rejection process (noise removal process). Therefore, the contrast of the synthesized image data 13 can be adjusted by the synthesis processing part 27 varying the threshold value of the rejection process (noise removal process) and adjusting the curve switching point 17.

The threshold value of the rejection process (noise removal process) may be input by an operator through a parameter acquisition interface (input part 7 etc.), or may be set to a value selected from a plurality of choices. Alternatively, a value of luminance to be removed may be calculated by setting an ROI, and the value may be used as the threshold value. Furthermore, a region of attention (e.g., the inside of the heart chamber) may be automatically detected and a value of luminance to be removed may be calculated to use that value as the threshold value.

When the sum of the synthetic ratio (first weighting factor) $\alpha$ and the synthetic ratio (second weighting factor) $\beta$ is larger than 1, i.e., $\alpha+\beta>1.0$", the effect of the present invention is more clearly confirmed. Difference in contrast of the synthesized image data 13 can be adjusted by the synthesis processing part 27 adjusting at least one of the synthetic ratio (first weighting factor) $\alpha$ and the synthetic ratio (second weighting factor) $\beta$.

The synthesis processing part 27 may adjust at least one of the synthetic ratio (first weighting factor) $\alpha$ and the synthetic ratio (second weighting factor) $\beta$ according to the region of the diagnosing object 9 on which the medical image data (ultrasound image data 10) is to be acquired. In ultrasound image data of the heart, for example, since image enhancement is required in the cardiac muscle where the luminance is relatively high (the range B where the luminance of input is high), signals in the cardiac muscle are enhanced through adjustment of the synthetic ratio (first weighting factor) $\alpha$, which makes the movement of the heart easier to see and favorably affects the diagnosis. On the inside of the heart chamber where the luminance is relatively low, since conspicuous noise causes degradation of the image quality, the noise inside the heart chamber can be made inconspicuous through adjustment (reduction) of the synthetic ratio (second weighting factor) $\beta$. Since the synthetic ratio (second weighting factor) $\beta$ is the synthetic ratio of the original image (ultrasound image data 10), it may be constant (e.g., "0.8").

As shown in FIG. 3, this embodiment may include a selection part 28 which selects at least one of the first weighting factor and the second weighting factor. The selection part 28 is a user interface which allows the operator to change the signal enhancement level, with difference in contrast being the signal enhancement level, and the synthesis processing part 27 may change the synthetic ratio (first weighting factor) $\alpha$ of the signal enhanced-noise rejected image data 12 and the synthetic ratio (second weighting factor) $\beta$ of the ultrasound image data 10 accordingly.

Figure 6:
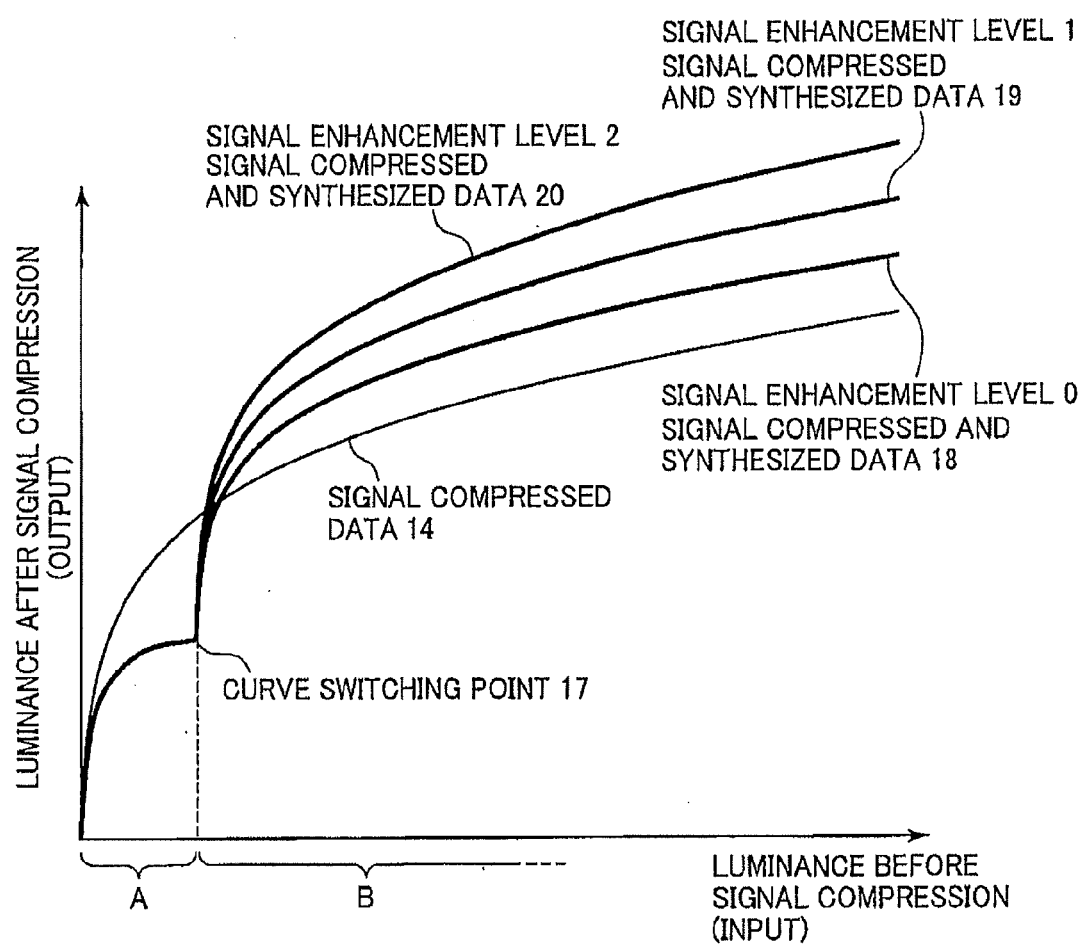
FIG. 6 is an example of comparison between signal compressed and synthesized data, for which the signal enhancement level is varied using the internal table of FIG. 5, and signal compressed data.

FIG. 5 shows one example of an internal table 31 which stores the synthetic ratio (first weighting factor) $\alpha$ of the signal enhanced-noise rejected image data 12 and the synthetic ratio (second weighting factor) $\beta$ of the ultrasound image data 10 corresponding to the respective signal enhancement levels. FIG. 6 is an example of comparison between the signal compressed and synthesized data 15, for which the signal enhancement level is varied using the internal table 31 of FIG. 5, and the signal compressed data 14.

As shown in FIG. 5, the ultrasound diagnostic apparatus (medical image processing apparatus) of this embodiment includes the internal table 31 which stores in advance at least one of the first weighting factor $\alpha$ and the second weighting factor $\beta$ corresponding to the signal enhancement levels ("0", "1", "2"). When a signal enhancement level is selected, at least one of the first weighting factor $\alpha$ and the second weighting factor $\beta$ corresponding to the selected signal enhancement level is selected from the internal table 31.

As shown in FIG. 6, if the signal enhancement level of FIG. 5 is raised and the synthetic ratio (first weighting factor) $\alpha$ is increased, the luminance of output (after signal compression) of the part of the signal compressed and synthesized data 15 where the luminance is higher than that of the signal compressed data 14 (the range B where the luminance is desired to be higher than that of the signal compressed data 14) becomes even higher. That is, the synthesis processing part 27 increases the synthetic ratio (first weighting factor) $\alpha$ such that, in the region of attention (e.g., the range B) of the diagnosing object 9, the luminance of the medical image data (signal compressed and synthesized data 15) synthesized by the synthesis processing part 27 becomes higher than the luminance of the medical image data (signal compressed data 14) on which the signal enhancement process and the rejection process (noise removal process) are not performed. In ultrasound image data of the heart, for example, since image enhancement is required in the cardiac muscle where the luminance is relatively high (the range B where the luminance of input is high), signals in the cardiac muscle are enhanced through adjustment (increase) of the synthetic ratio (first weighting factor) $\alpha$, which makes the movement of the heart easier to see and favorably affects the diagnosis.

While the embodiment according to the present invention has been described, the present invention is not limited thereto but can be changed or modified within the scope defined in the claims. For example, the values of the internal table 31 (signal enhancement levels) may be preset, and the operator may change the signal enhancement level on the basis of the internal table 31 through the signal enhancement level change interface (selection part 28). The value of the signal enhancement level may be input/selected by the operator through the parameter acquisition interface (input part 7, selection part 28, etc.).

An ROI can be set when it is desirable that the contrast enhancement process is not performed on regions or areas other than the region of attention. It is possible to avoid the enhancement process being performed on regions or areas, on which the contrast enhancement process is not desired to be performed, for example, by setting such that the high-contrast processing of this embodiment is performed inside the ROI while the high-contrast processing of this embodiment is not performed outside the ROI.

Second Embodiment

Figure 7:
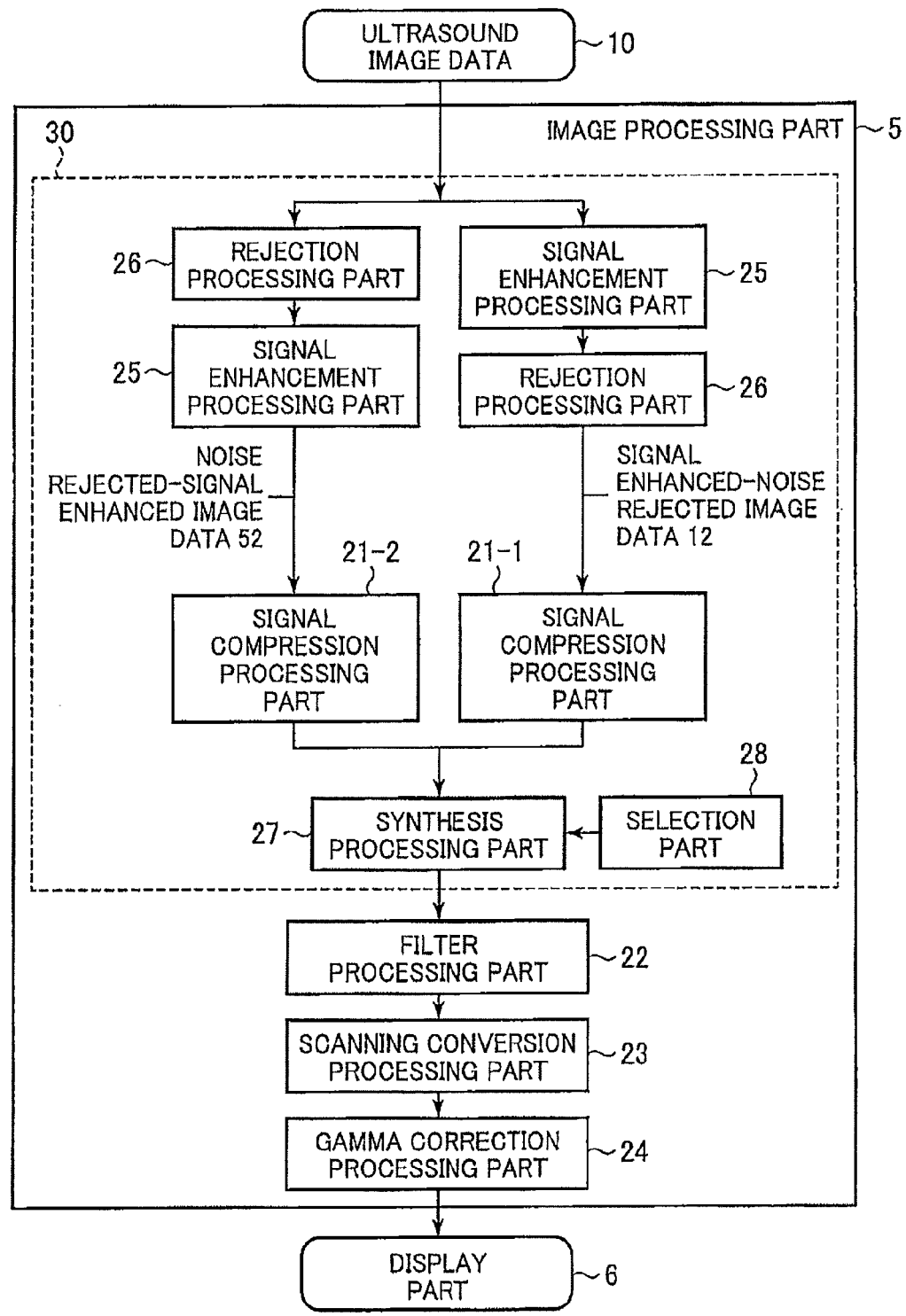
FIG. 7 is a block diagram showing one example of an ultrasound diagnostic apparatus which is a medical image processing apparatus of a second embodiment of the present invention.

Next, a medical image processing apparatus of a second embodiment of the present invention will be described using the drawings. FIG. 7 is a block diagram showing one example of an ultrasound diagnostic apparatus which is the medical image processing apparatus of the second embodiment of the present invention. In this embodiment, portions that are different from the first embodiment will be mainly described, while the other portions are the same as in the first embodiment. The components assigned the same reference signs as those of the first embodiment have the same function or working as in the first embodiment.

As shown in FIG. 7, the first signal compression processing part 21-1 compresses the medical image data (signal enhanced-noise rejected image data 12), on which the signal enhancement process has been performed and thereafter the rejection process (noise removal process) has been performed, and the second signal compression processing part 21-2 compresses the medical image data (noise rejected-signal enhanced image data 52), on which the rejection process (noise removal process) has been performed and thereafter the signal enhancement process has been performed. That is, in this embodiment, the rejection process (noise removal process) and the signal enhancement process are performed also on the original image, on which these processes are not performed in the first embodiment. It is possible to construct higher-contrast images by performing the rejection process and the signal enhancement process also on the original image.

Thus, the processing order of the rejection process (noise removal process) and the signal enhancement process may be changed according to the property of noise to be removed or the property of a structure in which signals are to be enhanced. The case where the rejection processing part (noise removal part) 26 performs the noise removal process after the signal enhancement processing part 25 performs the signal enhancement process on the medical image data (ultrasound image data 10) is characterized in that the noise is enhanced first and the noise may remain even after the noise removal process. On the other hand, the case where the signal enhancement processing part 25 performs the signal enhancement process after the rejection processing part (noise removal part) 26 performs the noise removal process on the medical image data (ultrasound image data 10) is characterized in that the noise is removed first and the signals in the region of attention in the original image may also be removed. Therefore, according to this embodiment, it is possible to complement both characteristics by changing the processing order of the rejection process (noise removal process) and the signal enhancement process, and to construct higher-contrast images while properly removing noise by the synthesis processing part 27 adjusting the synthetic ratio (first weighting factor) $\alpha$ and the synthetic ratio (second weighting factor) $\beta$.

Third Embodiment

Figure 8:
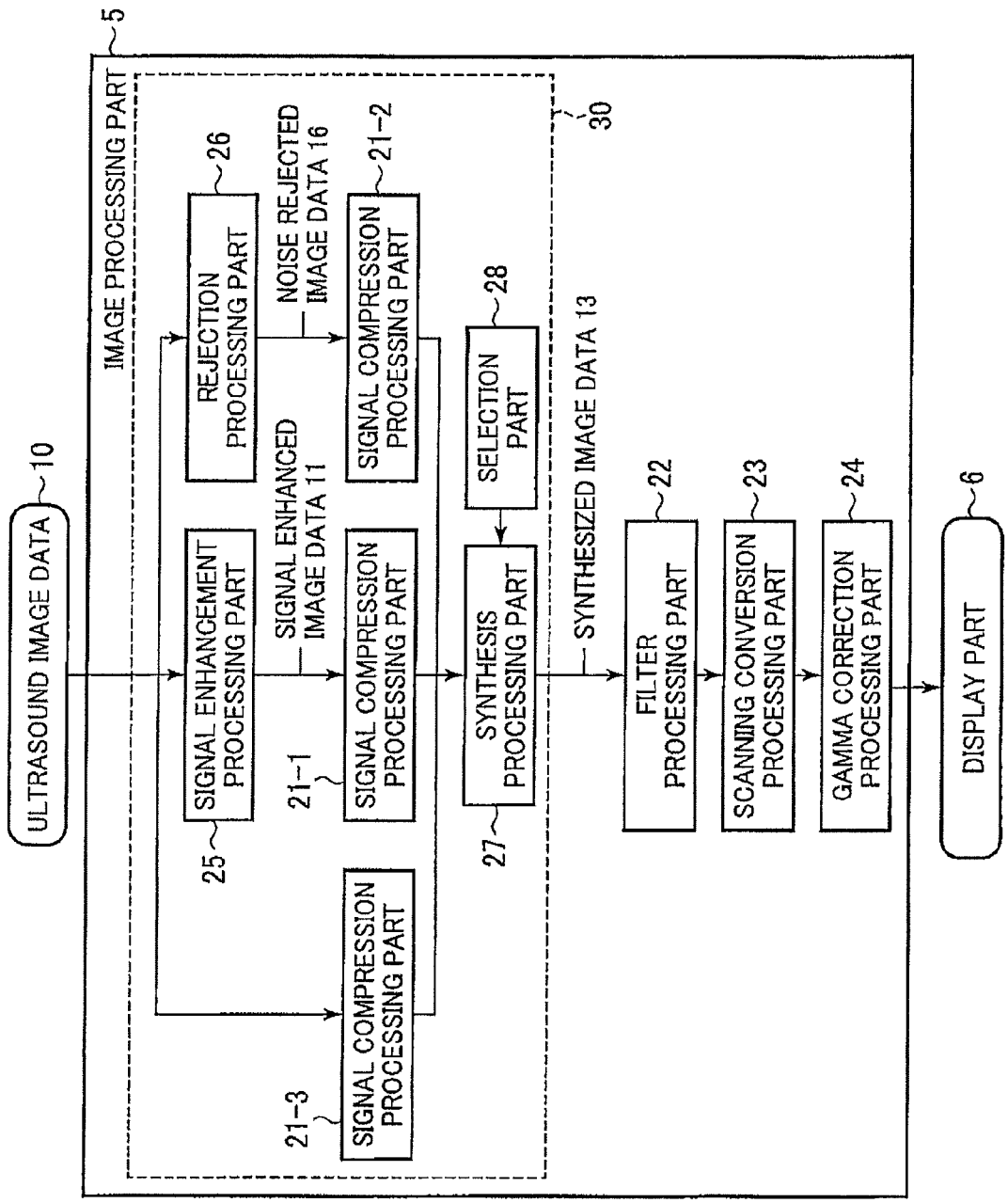
FIG. 8 is a block diagram showing one example of an ultrasound diagnostic apparatus which is a medical image processing apparatus of a third embodiment of the present invention.

Next, a medical image processing apparatus of a third embodiment of the present invention will be described using the drawings. FIG. 8 is a block diagram showing one example of an ultrasound diagnostic apparatus which is the medical image processing apparatus of the third embodiment of the present invention. In this embodiment, portions that are different from the first embodiment and the second embodiment will be mainly described, while the other portions are the same as in the first embodiment and the second embodiment. The components assigned the same reference signs as those of the first embodiment and the second embodiment have the same function or working as in the first embodiment and the second embodiment.

As shown in FIG. 8, the ultrasound diagnostic apparatus of this embodiment is a medical image processing apparatus which acquires medical image data on the diagnosing object 9, and includes: the signal enhancement processing part 25 which performs the signal enhancement process on the medical image data; the rejection processing part (noise removal part) 26 which performs the rejection process (noise removal process) on the medical image data; the first signal compression processing part 21-1 which compresses the medical image data on which the signal enhancement process has been performed; the second signal compression processing part 21-2 which compresses the medical image data on which the rejection process (noise removal process) has been performed; a third signal compression processing part 21-3 which compresses the medical image data on which the signal enhancement process and the rejection process (noise removal process) are not performed; and the synthesis processing part 27 which synthesizes the medical image data having been compressed in the first signal compression processing part 21-1, the medical image data having been compressed in the second signal compression processing part 21-2, and the medical image data having been compressed in the third signal compression processing part 21-3.

The signal enhancement processing part 25 performs the signal enhancement process on the ultrasound image data 10. The rejection processing part (noise removal part) 26 performs the rejection process (noise removal process) on the ultrasound image data 10. The signal enhancement process and the rejection process (noise removal process) are separately performed.

Thereafter, the first signal compression processing part 21-1 compresses the ultrasound image data (medical image data) 10 on which the signal enhancement process has been performed. The second signal compression processing part 21-2 compresses the ultrasound image data (medical image data) 10 on which the rejection process (noise removal process) has been performed. The third signal compression processing part 21-3 compresses the ultrasound image data (medical image data) 10 on which the signal enhancement process and the rejection process (noise removal process) are not performed. The respective signal compression processing parts 21-1, 21-2, and 21-3 perform the signal compression process on the three pieces of image data, the image data (signal enhanced image data 11) having been processed in the signal enhancement processing part 25, the image data (noise rejected image data 16) having been processed in the rejection processing 26, and the ultrasound image data 10.

After the signal compression process, the synthesis processing part 27 performs the synthesis process on the three pieces of image data on which the signal compression process has been performed, and generates the synthesized image data 13. In this embodiment, the synthesis processing part 27 multiplies the medical image data (signal enhanced image data 11), which has been compressed in the first signal compression processing part 21-1, by a first weighting factor, multiplies the medical image data (noise rejected image data 16), which has been compressed in the second signal compression processing part, by a second weighting factor, and multiplies the medical image data (ultrasound image data 10), which has been compressed in the third signal compression processing part, by a third weighting factor, to thereby synthesize the medical image data having been compressed in the first signal compression processing part 21-1, the medical image data having been compressed in the second signal compression processing part 21-2, and the medical image data having been compressed in the third signal compression processing part 21-3 and generate the synthesized image data 13.

When the synthesized image data 13 is "y", the signal enhanced image data 11 is "$x_e$", the noise rejected image data 16 is "$x_r$", and the ultrasound image data 10 is "x", the synthesis processing is expressed by the formula (2).

$$y = \alpha 1 \cdot x_e + \alpha 2 \cdot x_r + \beta \cdot x \quad (2)$$

Here, in the formula (2), α1 denotes the synthetic ratio (first weighting factor) of the signal enhanced image data 11, α2 denotes the synthetic ratio (second weighting factor) of the noise rejected image data 16, and β denotes the synthetic ratio (third weighting factor) of the ultrasound image data 10.

When the sum of the synthetic ratio (first weighting factor) α1, the synthetic ratio (second weighting factor) α2, and the synthetic ratio (third weighting factor) β is larger than 1, i.e., "α1+α2+β>1.0", the effect of the present invention is more clearly confirmed. It is possible to adjust the difference in contrast of the synthesized image data 13 by the synthesis processing part 27 adjusting at least one of the synthetic ratio (first weighting factor) α1, the synthetic ratio (second weighting factor) α2, and the synthetic ratio (third weighting factor) β.

The synthesis processing part 27 may adjust at least one of the synthetic ratio (first weighting factor) α1, the synthetic ratio (second weighting factor) α2, and the synthetic ratio (third weighting factor) β according to the region of the diagnosing object 9 on which the medical image data (ultrasound image data 10) is to be acquired. In ultrasound image data of the heart, for example, since image enhancement is required in the cardiac muscle where the luminance is relatively high (the range B where the luminance of input is high), signals in the cardiac muscle are enhanced through adjustment (increase) of the synthetic ratio (first weighting factor) α1, which makes the movement of the heart easier to see and favorably affects the diagnosis. On the inside of the heart chamber where the luminance is relatively low, since conspicuous noise causes degradation of the image quality, the noise inside the heart chamber can be made inconspicuous through adjustment (increase) of the synthetic ratio (second weighting factor) α2 and adjustment (reduction) of the synthetic ratio (third weighting factor) β.

Thus, it is possible to adjust the difference in contrast of the synthesized image data 13 by adjusting each of the synthetic ratios α1, α2, and β. The synthesis processing part 27 may change the synthetic ratio (first weighting factor) α1 of the signal enhanced image data 11, the synthetic ratio (second weighting factor) α2 of the noise rejected image data 16, and the synthetic ratio (third weighting factor) β of the ultrasound image data 10 by means of the selection part 28 which changes the signal enhancement level.

FIG. 9 is one example of an internal table 32 which stores the synthetic ratio (first weighting factor) α1 of the signal enhanced image data 11, the synthetic ratio (second weighting factor) α2 of the noise rejected image data 16, and the synthetic ratio (third weighting factor) β of the ultrasound image data 10 corresponding to the respective signal enhancement levels. As shown in FIG. 9, the ultrasound diagnostic apparatus (medical image processing apparatus) of this embodiment includes the internal table 32 which stores in advance at least one of the synthetic ratio (first weighting factor) α1, the synthetic ratio (second weighting factor) α2, and the synthetic ratio (third weighting factor) β corresponding to the signal enhancement levels ("0", "1", "2"). When a signal enhancement level is selected, at least one of the synthetic ratio (first weighting factor) α1, the synthetic ratio (second weighting factor) α2, and the synthetic ratio (third weighting factor) β corresponding to the selected signal enhancement level is selected from the internal table 32. The values of the internal table 32 (signal enhancement levels) may be preset, and the operator may change the signal enhancement level on the basis of the internal table 32 through the signal enhancement level change interface (selection part 28). The value of the signal enhancement level may be input/selected by the operator through the parameter acquisition interface (input part 7, selection part 28, etc.).

As shown in FIG. 9, the synthesis processing part 27 may reduce the synthetic ratio (third weighting factor) β such that, in a part (e.g., the range A of FIG. 4 or FIG. 6) where the luminance is lower than the luminance of the region of attention of the diagnosing object 9, the luminance of the medical image data (e.g., the signal compressed and synthesized data 15 of FIG. 4 or FIG. 6), which has been synthesized by the synthesis processing part 27, is lower than the luminance of the medical image data (e.g., the signal compressed data 14 of FIG. 4 or FIG. 6), which has been compressed without the signal enhancement process and the noise removal process performed on it.

While the embodiment according to the present invention has been described, the present invention is not limited thereto but can be changed or modified within the scope defined in the claims. For example, for the ultrasound image data 10 input from the signal processing part 4 of FIG. 1 to the image processing part 5, a larger number of pieces of image data than the three pieces of image data described above may be constructed, and the signal compression processing part 21 may perform the signal compression process on each piece of the image data, and thereafter the synthesis processing part 27 may synthesize the synthesized image data 13.

Thus, according to the first embodiment, the second embodiment, and the third embodiment of the present invention, it is possible to construct high-contrast medical images, in which noise can be removed while signals in a region of attention can be enhanced, by the signal compression and synthesis processing part 30 compressing the medical image data on which the signal enhancement process and/or the noise removal process have been performed and synthesizing the compressed medical image data.

While the embodiments according to the present invention have been described, the present invention is not limited thereto but can be changed or modified within the scope defined in the claims.

Figure 10:
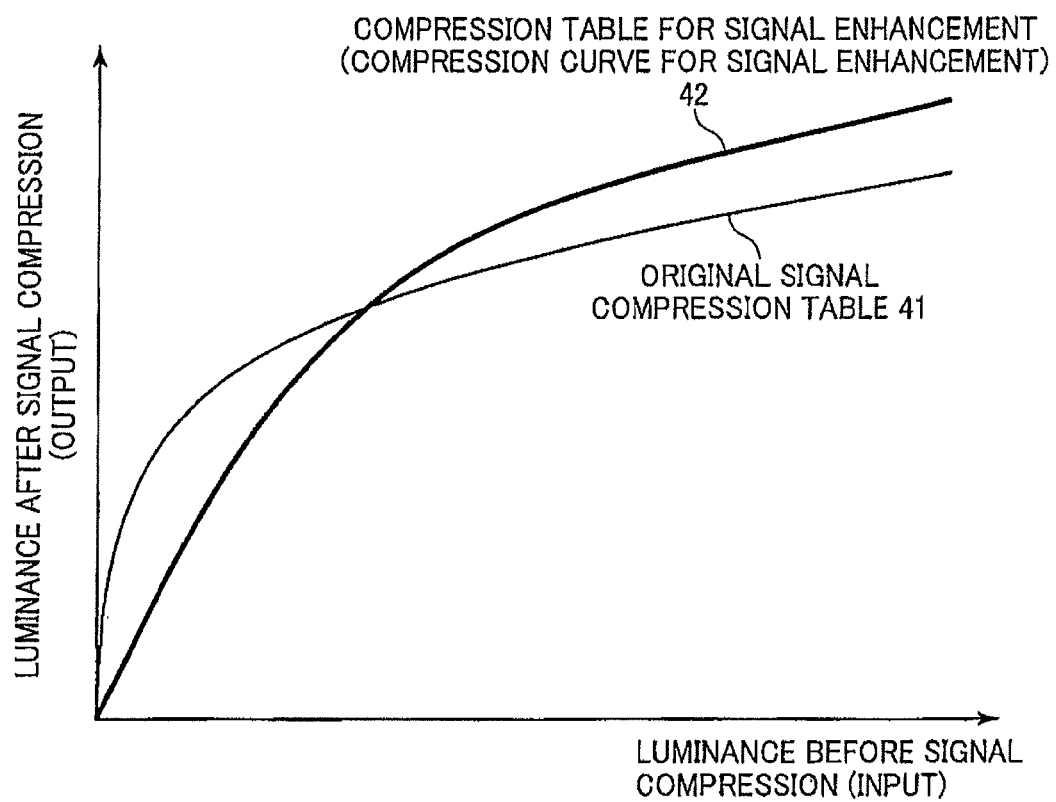
FIG. 10 is a view showing one example of a compression table for signal enhancement (compression curve for signal enhancement).

In the embodiments according to the present invention, a part where the luminance is low (e.g., the range A of FIG. 4) is reduced in luminance and a part where the luminance is high (e.g., the range B of FIG. 4) is further increased in luminance by performing the synthesis process after the signal compression process. When this signal compression process is performed, a compression table for signal enhancement (compression curve for signal enhancement) 42 as shown in FIG. 10 may be used. It is possible to enhance the contrast by using the compression table for signal enhancement (compression curve for signal enhancement) 42.

A plurality of compression tables for signal enhancement (compression curves for signal enhancement) 42 may be stored in a storage part, and a compression table for signal enhancement (compression curve for signal enhancement) 42 corresponding to a signal enhancement level selected by the operator through the signal enhancement level change interface (selection part 28) may be used to adjust the enhancement of contrast.

While in the embodiments according to the present invention, the ultrasound diagnostic apparatus has been described as the medical image processing apparatus, as long as it is a diagnostic apparatus capable of acquiring medical image data on a diagnosing object, the medical image processing apparatus may be an MRI diagnostic apparatus, an X-ray apparatus, a CT apparatus, etc.

INDUSTRIAL APPLICABILITY

The medical image processing apparatus according to the present invention has an effect that high-contrast medical images can be constructed in which noise can be removed while signals in a region of attention can be enhanced, and is useful as a medical image processing apparatus which displays high-contrast medical images.

REFERENCE SIGNS LIST

1 Ultrasound probe
2 Transmission/reception switching part
3 Beam formation part
4 Signal processing part
5 Image processing part
6 Display part
7 Input part
8 Control part
21 Signal compression processing part
22 Filter processing part
23 Scanning conversion processing part
24 Gamma correction processing part
25 Signal enhancement processing part
26 Rejection processing part
27 Synthesis processing part
28 Selection part
30 Signal compression and synthesis processing part

The invention claimed is:

1. A medical image processing apparatus which acquires medical image data on a diagnosing object, the apparatus comprising:
   a signal enhancement processing part which performs a signal enhancement process on the medical image data;
   a rejection processing part which performs a noise removal process on the medical image data;
   a first signal compression processing part which compresses the medical image data on which the signal enhancement process and the noise removal process have been performed;
   a second signal compression processing part which compresses the medical image data; and
   a synthesis processing part which synthesizes the medical image data having been compressed in the first signal compression processing part and the medical image data having been compressed in the second signal compression processing part,
   wherein the functions performed by the signal enhancement processing part, the rejection processing part, the first signal compression processing part, the second signal compression processing part, and the synthesis processing part are implemented under control of a central processing unit (CPU).

2. The medical image processing apparatus according to claim 1, wherein the first signal compression processing part compresses the medical image data on which the signal enhancement process has been performed and thereafter the noise removal process has been performed.

3. The medical image processing apparatus according to claim 1, wherein the second signal compression processing part compresses the medical image data on which the signal enhancement process and the noise removal process are not performed.

4. The medical image processing apparatus according to claim 1, wherein the first signal compression processing part and the second signal compression processing part compress the medical image data by a same compression method at a same compression ratio.

5. The medical image processing apparatus according to claim 1, wherein
   the synthesis processing part multiplies the medical image data, which has been compressed in the first signal compression processing part, by a first weighting factor, and multiplies the medical image data, which has been compressed in the second signal compression processing part, by a second weighting factor, to thereby synthesize the medical image data having been compressed in the first signal compression processing part and the medical image data having been compressed in the second signal compression processing part, and
   a sum of the first weighting factor and the second weighting factor is larger than 1.

6. The medical image processing apparatus according to claim 5, wherein the synthesis processing part adjusts at least one of the first weighting factor and the second weighting factor according to a region of the diagnosing object on which the medical image data is to be acquired.

7. The medical image processing apparatus according to claim 5, wherein the synthesis processing part increases the first weighting factor such that, in a region of attention of the diagnosing object, a luminance of the medical image data which has been synthesized by the synthesis processing part is higher than a luminance of the medical image data which has been compressed without having been subjected to the signal enhancement process and the noise removal process.

8. The medical image processing apparatus according to claim 5, wherein the synthesis processing part reduces the second weighting factor such that, in a part lower in luminance than the region of attention of the diagnosing object, the luminance of the medical image data which has been synthesized by the synthesis processing part is lower than the luminance of the medical image data which has been compressed without having been subjected to the signal enhancement process and the noise removal process.

9. The medical image processing apparatus according to claim 5, further comprising:
   a selection part which selects at least one of the first weighting factor and the second weighting factor,
   wherein the functions performed by the selection part are implemented under control of the CPU.

10. The medical image processing apparatus according to claim 5, further comprising:
    an internal table which stores in advance at least one of the first weighting factor and the second weighting factor corresponding to signal enhancement levels,
    wherein the internal table is a storage.

11. The medical image processing apparatus according to claim 10, wherein, when one of the signal enhancement levels is selected, at least one of the first weighting factor and the second weighting factor corresponding to the selected signal enhancement level is selected from the internal table.

12. The medical image processing apparatus according to claim 1, wherein
    the first signal compression processing part compresses the medical image data on which the signal enhancement process has been performed and thereafter the noise removal process has been performed, and the second signal compression processing part compresses the medical image data on which the noise removal process has been performed and thereafter the signal enhancement process has been performed.

13. A medical image processing apparatus which acquires medical image data on a diagnosing object, the apparatus comprising:
   a signal enhancement processing part which performs a signal enhancement process on the medical image data;
   a rejection processing part which performs a noise removal process on the medical image data;
   a first signal compression processing part which compresses the medical image data on which the signal enhancement process has been performed;
   a second signal compression processing part which compresses the medical image data on which the noise removal process has been performed;
   a third signal compression processing part which compresses the medical image data on which the signal enhancement process and the noise removal process are not performed; and
   a synthesis processing part which synthesizes the medical image data having been compressed in the first signal compression processing part, the medical image data having been compressed in the second signal compression processing part, and the medical image data having been compressed in the third signal compression processing part,
   wherein the functions performed by the signal enhancement processing part, the rejection processing part, the first signal compression processing part, the second signal compression processing part, the third signal compression processing part, and the synthesis processing part are implemented under control of a central processing unit (CPU).

14. A medical image generation method for acquiring medical image data on a diagnosing object, the method comprising:
   performing a signal enhancement process on the medical image data;
   performing a noise removal process on the medical image data;
   performing a first signal compression process of compressing the medical image data on which the signal enhancement process and the noise removal process have been performed;
   performing a second signal compression process of compressing the medical image data; and
   synthesizing the medical image data having been compressed in the first signal compression process and the medical image data having been compressed in the second signal compression process.

* * * * *